United States Patent [19]

Evans

[11] Patent Number: 5,246,606
[45] Date of Patent: Sep. 21, 1993

[54] PROCESS OF STABILIZING LUBRICANTS, OR FUNCTIONAL FLUIDS AND A COMPOSITION THEREFOR

[75] Inventor: Samuel Evans, Marly, Switzerland

[73] Assignee: Ciba-Geigy Corporation, Ardsley, N.Y.

[21] Appl. No.: 825,676

[22] Filed: Jan. 27, 1992

[30] Foreign Application Priority Data

Jan. 31, 1991 [CH] Switzerland ............... 290/91

[51] Int. Cl.[5] .......................... C10M 105/56
[52] U.S. Cl. .................. 252/47.5; 252/50; 252/51; 546/165; 546/166
[58] Field of Search ............ 252/47.5, 50, 51

[56] References Cited

U.S. PATENT DOCUMENTS

| | | | |
|---|---|---|---|
| 3,870,574 | 3/1975 | Stefán et al. | 148/122 |
| 4,025,631 | 5/1977 | Bär et al. | 252/401 |
| 4,046,765 | 9/1977 | Bär et al. | 546/165 |
| 4,069,195 | 1/1978 | Layer et al. | 546/166 |
| 4,244,864 | 1/1981 | Campbell et al. | 546/166 |
| 4,692,258 | 9/1987 | Rasberger et al. | 252/50 |
| 4,828,741 | 5/1989 | Meier et al. | 252/51.5 |

FOREIGN PATENT DOCUMENTS

| | | |
|---|---|---|
| 2832126 | 8/1981 | Fed. Rep. of Germany . |
| 3540105 | 5/1986 | Fed. Rep. of Germany . |
| 155212 | 5/1982 | German Democratic Rep. . |
| WO87/00048 | 1/1987 | PCT Int'l Appl. . |
| WO88/08420 | 11/1988 | PCT Int'l Appl. . |
| 2166953 | 5/1986 | United Kingdom . |

OTHER PUBLICATIONS

Derwent Abstract 24364D/14 (Feb. 1981).
Derwent WPI Acc. No.: 79-12274B/07 (1979).
Abst. for German 3540105.

*Primary Examiner*—C. Warren Ivy
*Assistant Examiner*—James H. Turnipseed
*Attorney, Agent, or Firm*—Luther A. R. Hall

[57] ABSTRACT

Novel substituted tetrahydroquinoline compounds of the formula I

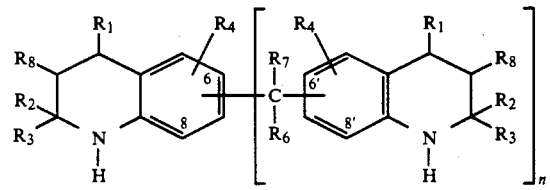

are described, in which $R_1$ is $C_{1-18}$alkyl or together with $R_8$ 1,4-butylene, $R_2$ and $R_3$, independently of one another, are $C_{1-18}$alkyl, phenyl or phenyl-$C_{1-4}$alkyl or together tetra-, penta- or hexamethylene, $R_4$ is hydrogen, halogen, nitro, $C_{1-24}$alkyl or a group of the formula —O—$R_5$, $R_5$ is hydrogen, $C_{1-18}$alkyl or benzyl, $R_6$ and $R_7$, independently of one another, are hydrogen, $C_{1-18}$alkyl, $C_{2-18}$alkyl which is interrupted by —S— or —O—, or are phenyl or phenyl-$C_{1-4}$alkyl or together $C_{4-11}$alkylene, $R_8$ is hydrogen, $C_{1-18}$alkyl or together with $R_1$ 1,4-butylene, and n is 1,2 or 3. The compounds are suitable as stabilisers, in particular as antioxidants for organic materials.

6 Claims, No Drawings

PROCESS OF STABILIZING LUBRICANTS, OR FUNCTIONAL FLUIDS AND A COMPOSITION THEREFOR

The invention relates to novel hydroquinoline compounds, to compositions containing them and to the use of these compounds as stabilisers for organic material.

Dihydroquinoline derivatives of the formula

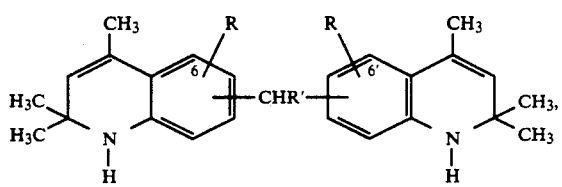

in which R' is hydrogen or alkyl having 1 to 4 C atoms and R is methyl which is not bound to C6 or C6', are disclosed in DE-A-2 243 777 as antioxidants for industrial products, in particular natural and synthetic rubber products. Later, compounds of this basic structure were also proposed as preservatives for feedstuffs (DE-A-3 540 195, WO-A-87/00 048, WO-A-88/08 420) and in combination with organic halides as colour formers in photosensitive recording materials (DD-A-155 212). Furthermore, tetrahydroquinoline compounds are disclosed in U.S. Pat. Nos. 4,692,258 and 4,828,741 as stabilisers for lubricants.

Surprisingly, it has now been found that dimeric, trimeric and tetrameric tetrahydroquinoline derivatives are particularly suitable as stabilisers for organic material.

Accordingly, the invention relates to compounds of the formula I

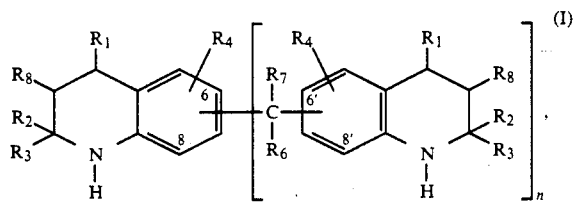

in which $R_1$ is $C_{1-18}$alkyl or together with $R_8$ 1,4-butylene, $R_2$ and $R_3$, independently of one another, are $C_{1-18}$alkyl, phenyl or phenyl-$C_{1-4}$alkyl or together tetra-, penta- or hexamethylene, $R_4$ is hydrogen, halogen, nitro, $C_{1-24}$alkyl or a group of the formula —O—$R_5$, $R_5$ is hydrogen, $C_{1-18}$alkyl or benzyl, $R_6$ and $R_7$, independently of one another, are hydrogen, $C_{1-18}$alkyl, $C_{2-18}$alkyl which is interrupted by —S— or —O—, or are phenyl or phenyl-$C_{1-4}$alkyl or together $C_{4-11}$alkylene, $R_8$ is hydrogen, $C_{1-18}$alkyl or together with $R_1$ 1,4-butylene, and n is 1, 2 or 3. Preferably, n is 1 or 2, in particular 1.

$R_1$, $R_2$, $R_3$, $R_4$, $R_6$, $R_7$ and $R_8$ as $C_{1-18}$alkyl or $C_{1-24}$alkyl can be straight-chained or branched and are, for example, methyl, ethyl, propyl, isopropyl, n-butyl, isobutyl, t-butyl, pentyl, isopentyl, hexyl, heptyl, 3-octyl, 2-ethylhexyl, nonyl, decyl, undecyl, dodecyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl, 1-methylundecyl or additionally also, for example, eicosyl or henicosyl. Where these radicals are groups having a relatively small number of C atoms, corresponding examples may also be taken from the above list. Where the radicals mentioned are alkyl, they have preferably 1-12, in particular 1-6, especially 1-4 C atoms. Where $R_6$ and $R_7$ are interrupted by —O— or —S—, they may contain one or more of the heteroatoms and, for example, the groups —$CH_2$—$CH_2$—O— and —$CH_2$—$CH_2$—S— are present therein, if desired, next to one another. Interruption by a single O or S atom is preferred.

Where any of these radicals together form alkylene, they can, for example, be a linear or branched, preferably linear, alkylene. Examples of these radicals can be taken from the above examples of $C_{1-18}$alkyl having the corresponding number of C atoms by adding the suffix -ene. Preferably, $R_6$ and $R_7$ together are tetra-, penta- and hexamethylene, in particular pentamethylene.

Examples of $R_2$, $R_3$, $R_6$ and $R_7$ as phenyl-$C_1$-$C_4$alkyl are benzyl, phenethyl, 3-phenylpropyl, α-methylbenzyl or α,α-dimethylbenzyl. Benzyl is preferred.

$R_4$ and $R_8$ are preferably hydrogen.

Preferred compounds of the formula I are those in which $R_1$ is $C_{1-8}$alkyl, $R_2$ and $R_3$, independently of one another, are $C_{1-8}$alkyl, phenyl, benzyl or cyclohexyl, $R_4$ is hydrogen, $C_{1-12}$alkyl, hydroxyl, methoxy or ethoxy, $R_6$ and $R_7$ are hydrogen, $C_{1-12}$alkyl, phenyl or together pentamethylene, and $R_8$ is hydrogen.

Those compounds of the formula I, in which $R_1$, $R_2$ and $R_3$ are methyl, $R_4$ is hydrogen or $C_{1-12}$alkyl, $R_6$ is hydrogen or $C_{1-12}$alkyl, $R_7$ is hydrogen, methyl, ethyl or phenyl, $R_8$ is hydrogen, and n is 1, $R_4$, $R_6$, $R_7$ and $R_8$ being in particular hydrogen, are also preferred.

$R_4$ in formula I is preferably in the 6(6') or 8(8') positions, and the group

in the case where n=1, preferably links the 8 and 8' or 6 and 6' positions. Particularly preferably, $R_4$ is in the 6(6') position.

Where $R_4$ is hydrogen and n is 1, the group

preferably links the C atoms 6 and 6'.

In the case where n=2, the radicals

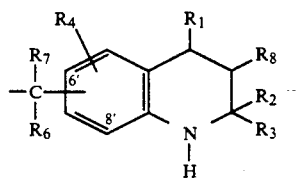

preferably occupy the 6 and 8 positions.

In particularly preferred compounds of the formula I, $R_1$, $R_2$ and $R_3$ are methyl, $R_4$, $R_6$ and $R_8$ are hydrogen, $R_7$ is hydrogen, phenyl or $C_6$-$C_{18}$alkyl, n is 1, and the group

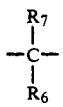

is linked with C atoms 6 and 6'.

The compounds of the formula I are highly suitable for stabilising organic materials against light-induced, thermal or/and oxidative degradation. Accordingly, the invention also relates to compositions containing an organic material which is sensitive to degradation reactions of this type and at least one compound of the formula I, or to the use of compounds of the formula I as stabilisers for organic materials against the types of degradation mentioned.

The compounds of the formula I can be used in particular as stabilisers for natural, semi-synthetic or synthetic polymers, in particular thermoplastics and elastomers, and for functional liquids, in particular lubricants and hydraulic fluids. Examples of substrates of this type can be taken from the following listing of suitable materials.

1. Polymers of monoolefins and diolefins, for example polypropylene, polyisobutylene, polybut-1-ene, polymethylpent-1-ene, polyisoprene or polybutadiene, and also polymers of cycloolefins, for example of cyclopentene or norbornene; as well as polyethylene (which if desired can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as ethylene/propylene copolymers, linear low-density polyethylene (LLDPE) and mixtures thereof with low-density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and their salts (ionomers), and terpolymers of ethylene with propylene and a diene, such as hexadiene, dicyclopentadiene or ethylidenenorbornene; as well as mixtures of such copolymers with each other and with polymers mentioned under 1), for example polypropylene/ethylene-propylene copolymers, LDPE/ethylene-vinyl acetate copolymers, LDPE/ethylene-acrylic acid copolymers, LLDPE/ethylene-vinyl acetate copolymers and LLDPE/ethylene-acrylic acid copolymers.

3a. Random or alternating copolymers of α-olefins with carbon monoxide.

3b. Hydrocarbon resins (for example $C_5$–$C_9$) and hydrogenated modifications thereof (for example tackifier resins).

4. Polystyrene, poly(p-methylstyrene), poly(α-methylstyrene).

5. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/maleic anhydride, styrene/acrylonitrile/methyl acrylate; mixtures of high impact strength from copolymers of styrene and another polymer, for example from a polyacrylate, a diene polymer or an ethylene/propylene/diene terpolymer; and block copolymers of styrene, for example styrene/butadiene/styrene, styrene/isoprene/styrene, styrene/ethylene-butylene/styrene or styrene/ethylene-propylene/styrene.

6. Graft copolymers of styrene or α-methylstyrene, for example styrene on polybutadiene; styrene on copolymers of polybutadiene-styrene or polybutadiene-acrylonitrile; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or alkyl methacrylates on polybutadiene; styrene and acrylonitrile on ethylene/propylene/diene terpolymers; styrene and acrylonitrile on polyalkyl acrylates or poly(alkyl methacrylates); styrene and acrylonitrile on acrylate/butadiene copolymers, and also mixtures thereof with the copolymers mentioned under 5), for example those known as ABS, MBS, ASA and AES polymers.

7. Halogen-containing polymers, such as polychloroprene, chlorinated rubber, chlorinated or chlorosulfonated polyethylene, copolymers of ethylene and chlorinated ethylene, epichlorohydrin homo- and copolymers, in particular polymers from halogen-containing vinyl compounds, for example polyvinyl chloride, polyvinylidene chloride, polyvinyl fluoride, polyvinylidene fluoride; and also copolymers thereof, such as vinyl chloride/vinylidene chloride, vinyl chloride/vinyl acetate or vinylidene chloride/vinyl acetate.

8. Polymers which are derived from α,β-unsaturated acids and derivatives thereof, such as polyacrylates and polymethacrylates, polyacrylamides and polyacrylonitriles.

9. Copolymers of the monomers mentioned under 8) with each other or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

10. Polymers which are derived from unsaturated alcohols and amines, or acyl derivatives or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; and also their copolymers with olefins mentioned in section 1.

11. Homopolymers and copolymers of cyclic ethers, such as polyalkylene glycols, polyethylene oxide, polypropylene oxide or copolymers thereof with bisglycidyl ethers.

12. Polyacetals such as polyoxymethylene, and also those polyoxymethylenes which contain comonomers, for example ethylene oxide; polyacetals modified with thermoplastic polyurethanes, acrylates or MBS.

13. Polyphenylene oxides and sulfides and mixtures thereof with styrene polymers or polyamides.

14. Polyurethanes which are derived from polyethers, polyesters and polybutadienes with terminal hydroxyl groups on the one hand and aliphatic or aromatic polyisocyanates on the other hand, and also precursors thereof.

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained starting from m-xylene, diamine and adipic acid; polyamides prepared from hexamethylenediamine and isophthalic and/or terephthalic acid and if desired an elastomer as modifier, for example poly-2,4,4-trimethylhexamethylene terephthalamide or poly-m-phenyleneisophthalamide. Block copolymers of the aforementioned polyamides with polyolefins, olefin copolymers, ionomers or chemically bonded or grafted elastomers; or with polyethers, for example with polyethylene glycol, polypropylene glycol or polytetramethylene glycol. In addition, polyamides or copolyamides modified with EPDM or ABS; and also polyamides condensed during processing (RIM polyamide systems).

16. Polyureas, polyimides, polyamidoimides and polybenzimidazoles.

17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, and also block polyether esters derived from polyethers having hydroxyl end groups; in addition polyesters modified with polycarbonates or MBS.

18. Polycarbonates and polyester carbonates.

19. Polysulfones, polyether sulfones and polyether ketones.

20. Crosslinked polymers which are derived from aldehydes on the one hand and from phenols, urea or melamine on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols, and vinyl compounds as crosslinking agents, and also halogen-containing modifications thereof of low flammability.

23. Crosslinkable acrylic resins which are derived from substituted acrylic esters, for example from epoxy acrylates, urethane acrylates or polyester acrylates.

24. Alkyd resins, polyester resins and acrylate resins which are crosslinked with melamine resins, urea resins, polyisocyanates or epoxy resins.

25. Crosslinked epoxy resins which are derived from polyepoxides, for example from bisglycidyl ethers or from cycloaliphatic diepoxides.

26. Natural polymers, such as cellulose, rubber, gelatin and derivatives thereof which are chemically modified in a polymer-homologous manner, such as cellulose acetates, cellulose propionates and cellulose butyrates, or cellulose ethers, such as methylcellulose; and rosins and their derivatives.

27. Mixtures (polyblends) of the polymers mentioned above, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP or PA/PPO.

28. Natural and synthetic organic materials which are pure monomeric compounds or mixtures of such compounds, for example mineral oils, animal or vegetable fats, oil and waxes, or oils, waxes and fats based on synthetic esters (e.g. phthalates, adipates, phosphates or trimellitates) and also mixtures of synthetic esters with mineral oils in any desired weight ratio, which mixtures may, for example, be used as spinning preparations, and also aqueous emulsions thereof.

29. Aqueous emulsions of natural or synthetic rubbers, for example natural latex or latices of carboxylated styrene/butadiene copolymers.

In the compositions according to the invention, the compounds of the formula I are advantageously present in an amount of 0.01 to 10, for example 0.05 to 5, preferably 0.05 to 3, but in particular 0.1 to 2% by weight. One or more of these compounds of the formula I can be present, and the percentages by weight given relate to the entire amount of these compounds. The basis for calculation is the total weight of the organic material without the compounds of the formula I.

Incorporation into the materials can be carried out, for example, by mixing in or applying the compounds of the formula I and, if desired, other additives by the methods customary in industry. In the case of polymers, in particular synthetic polymers, incorporation can be carried out before or during moulding, or by applying the dissolved or dispersed compounds to the polymer, if appropriate with subsequent evaporation of the solvent. In the case of elastomers, these can also be stabilised as latices. A further possibility for incorporation of the compounds of the formula I in polymers comprises their addition before, during or immediately after polymerisation of the corresponding monomers or before crosslinking. The compounds of the formula I can be added as such, but also in encapsulated form (e.g. in waxes, oils or polymers). In the case of addition before or during polymerisation, the compounds of the formula I can also act as regulators for the chain length of the polymers (chain terminators).

The compounds of the formula I or mixtures thereof can also be added to the plastics to be stabilised in the form of a masterbatch which contains these compounds, for example in a concentration of 2.5 to 25% by weight.

The incorporation of the compounds of the formula I can advantageously be carried out by the following methods:
as an emulsion or dispersion (for example to give latices or emulsion polymers)
as a dry mixture during mixing of additive components or polymer mixtures
by direct addition to the processing apparatus (for example extruders, internal mixers etc.)
as a solution or melt.

Polymer compositions according to the invention can be used in various forms or processed into various products, for example as (into) films, fibers, tapes, moulded materials or profiles, or as binders for paints, adhesives or cements.

The invention also relates to a process for stabilising organic material, in particular thermoplastic polymers, elastomers or functional fluids, in particular lubricants, against oxidative, thermal and/or light-induced degradation, which process comprises adding compounds of the formula I to this material as stabilisers or applying them thereto.

The compounds of the formula I are, for example, particularly suitable for giving functional fluids improved use properties. In particular, their surprisingly good action as antioxidants may be mentioned. Accordingly, the invention also comprises compositions containing a functional fluid and at least one compound of the general formula I, as described above.

Examples of suitable functional fluids are lubricants, hydraulic fluids and metalworking fluids.

Suitable lubricants are based, for example, on mineral or synthetic oils or mixtures thereof or on vegetable or animal oils, fats and waxes. The lubricants are familiar to the person skilled in the art and are described in the relevant specialist literature, for example in Dieter Klamann, "Schmierstoffe und verwandte Produkte" [Lubricants and Related Products] (Verlag Chemie, Weinheim, 1982), in Schewe-Kobek, "Das Schmiermittel-Taschenbuch" [The Lubricant Handbook] (Dr. Alfred Hüthig-Verlag, Heidelberg, 1974) and in "Ullmanns Enzyklopädie der technischen Chemie" [Ullmann's Encyclopaedia of Industrial Chemistry], vol. 13, pages 85–94 (Verlag Chemie, Weinheim, 1977).

The lubricants are in particular oils and fats, for example based on a mineral oil. Oils are preferred.

The mineral oils are based in particular on hydrocarbon compounds.

Examples of synthetic lubricants include lubricants based on aliphatic or aromatic carboxylic esters, polymeric esters, polyalkylene oxides, phosphoric acid esters, poly-α-olefins or silicones, on a diester of a dibasic acid with a monohydric alcohol, for example dioctyl sebacate or dinonyl adipate, on a triester of trimethylolpropane with a monobasic acid or with a mixture of such acids, for example trimethylolpropane tripelargonate, trimethylolpropane tricaprylate or mixtures thereof, on a tetraester of pentaerythritol with a monobasic acid or with a mixture of such acids, for example pentaerythritol tetracaprylate, or on a complex ester of monobasic and dibasic acids with polyhydric alcohols, for example a complex ester of trimethylolpropane with caprylic and sebacic acid or of a mixture thereof. Particularly suitable in addition to mineral oils are, for example, poly-α-olefins, lubricants based on esters, phosphates, glycols, polyglycols and polyalkylene glycols and mixtures thereof with water.

Suitable vegetable lubricants are the oils, fats and waxes obtained, for example, from olives, palms, palm kernels, beet, rape, linseed, nuts, soyabeans, cotton, ricinus, sunflowers, pumpkin seeds, coconut, maize or modified forms thereof, for example sulfurised or epoxidised oils, such as epoxidised soyabean oil, and mixtures of the substances. Examples of animal oils, fats and waxes which can be used as lubricants are tallows, fish oils, sperm oil, neat's foot oil, cod-liver oils and lard oils and modified forms and mixtures thereof.

Metalworking fluids such as rolling, drawing and cutting oils are based in most cases on the mineral and synthetic oils described above and can also be present as oil-in-water or water-in-oil emulsions. The same applies to hydraulic fluids. Examples of further suitable functional fluids are compressor oils and spinning preparations.

The compounds of the formula I, as described above, can be for example present in the functional fluid in amounts of 0.01 to 10% by weight, advantageously in amounts of 0.03 to 5% by weight, preferably in an amount of 0.05 to 3% by weight and very particularly preferably of 0.5 to 1.5% by weight, relative to the composition.

The compounds of the formula I can be admixed to the functional fluid in a manner known per se. The compounds are, for example, readily soluble in oils. It is also possible to prepare a so-called masterbatch, which can be diluted as it is consumed to the concentrations used using the corresponding functional fluid.

In addition to the compounds or mixtures according to the invention, the compositions according to the invention can contain further customary additives, in particular if they contain organic, preferably synthetic, polymers. Examples of additives of this type are:

1. Antioxidants 1.1. Alkylated monophenols, for example 2,6-di-tert-butyl-4-methylphenol, 2,6-di-tert-butylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, o-tert-butylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-or -5-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-di(3-tert-butyl-5-methyl-2-hydroxybenzyl)-4-methylphenol, 1,1,3-tris(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl] terephthalate.

1.5. Benzyl compounds, for example 1,3,5-tri(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithioterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate.

1.6. Acylaminophenols, for example lauric acid 4-hydroxyanilide, stearic acid 4-hydroxyanilide, 2,4-bis-(octylmercapto)-6-(3,5-di-tert-butyl-4-hydroxyanilino)-s-triazine, octyl N-(3,5-di-tert-butyl-4-hydroxyphenyl)-carbamate.

1.7. Esters of β-(3,5-di-tert-butyl-4-hydroxyphenyl)-propionic acid with mono- or polyhydric alcohols, e.g. with methanol, octadecanol, 1,6-hexanediol, neopentyl glycol, thiodiethylene glycol, diethylene glycol, triethylene glycol, pentaerythritol, tris(hydroxyethyl) isocyanurate, N,N'-bis(hydroxyethyl)oxalamide.

1.8. Esters of β-(5-tert-butyl-4-hydroxy-3-methylphenyl)propionic acid with mono- or polyhydric alcohols, e.g. with methanol, octadecanol, 1,6-hexanediol, neopentyl glycol, thiodiethylene glycol, diethylene glycol, triethylene glycol, pentaerythritol, tris(hydroxyethyl) isocyanurate, N,N'-bis(hydroxyethyl)oxalamide.

1.9. Esters of β-(3,5-dicyclohexyl-4-hydroxyphenyl)-propionic acid with mono- or polyhydric alcohols, e.g. with methanol, octadecanol, 1,6-hexanediol, neopentyl glycol, thiodiethylene glycol, diethylene glycol, triethylene glycol, pentaerythritol, tris(hydroxyethyl) isocyanurate, N,N'-bis(hydroxyethyl)oxalamide.

1.10. Amides of β-(3,5-di-tert-butyl-4-hydroxyphenyl)propionic acid, for example N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis(α,α-dimethylbenzyl) derivative.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of substituted or unsubstituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of monoalkyl 4-hydroxy-3,5-di-tert-butylbenzylphosphonates, such as of the methyl or ethyl ester, nickel complexes of ketoximes, such as of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetracarboxylate, 1,1'-(1,2-ethanediyl)bis(3,3,5,5-tetramethylpiperazinone).

2.7. Oxalamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide, and mixtures of o- and p-methoxy-disubstituted oxanilides and also o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxalamide N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylenediphosphonite, 3,9-bis(2,4-di-tert-butylphenoxy)-2,4,8,10-tetraoxa-3,9-diphosphaspiro[5.5]undecane.

5. Compounds which destroy peroxides, for example esters of β-thiodipropionic acid, for example the lauryl, stearyl, myristyl or tridecyl esters, mercaptobenzimidazole, or the zinc salt of 2-mercaptobenzimidazole, zinc dibutyldithiocarbamate, dioctadecyl disulfide, pentaerythritol tetrakis(β-dodecylmercapto)-propionate.

6. Polyamide stabilisers, for example copper salts in combination with iodides and/or phosphorus compounds and salts of divalent manganese.

7. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium stearate, sodium ricinoleate and potassium palmitate, antimony pyrocatecholate or tin pyrocatecholate.

8. Nucleating agents, for example 4-tert-butylbenzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticisers, lubricants, emulsifiers, pigments, fluorescent whitening agents, flameproofing agents, antistatic agents and blowing agents.

If the compositions according to the invention are those based on functional fluids, in particular lubricants and hydraulic fluids or metalworking fluids, they can also contain other additives which are added to improve certain use properties, for example other antioxidants, metal deactivators, rust inhibitors, viscosity index improvers, pour point depressants, dispersants/surfactants and wear-resistant additives.

Examples of phenolic antioxidants: these may be taken from the above sections 1.1 to 1.10.

Examples of amine antioxidants:
N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-di(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-napthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, di(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-di[(2-methylphenyl)amino]ethane, 1,2-di(-phenylamino)propane, (o-tolyl)biguanide, di[4-(1',3'-dimethylbutyl)phenyl]amine, tert-octylated N-phenyl-1-naphthylamine, mixture of mono- and dialkylated tert-butyl/tert-octyldiphenylamines, 2,3-dihydro-3,3-dimethyl-4H-1,4-benzothiazine, phenothiazine, N-allylphenothiazine.

Examples of other antioxidants: aliphatic or aromatic phosphites, esters of thiodipropionic acid or thiodiacetic acid, or salts of dithiocarbamic or dithiophosphoric acid.

Examples of metal deactivators, for example for copper, are: triazoles, benzotriazoles and derivatives thereof, tolutriazoles and derivatives thereof, 2-mercaptobenzothiazole, 2-mercaptobenzotriazole, 2,5-dimercaptobenzotriazole, 2,5-dimercaptobenzothiadiazole, 5,5'-methylenebisbenzotriazole, 4,5,6,7-tetrahydrobenzotriazole, salicylidenepropylenediamine, salicylaminoguanidine and salts thereof.

Examples of rust inhibitors are:
a) Organic acids, their esters, metal salts and anhydrides, for example: N-oleoylsarcosine, sorbitan monooleate, lead naphthenate, alkenylsuccinic anhydride, for example dodecenylsuccinic anhydride, alkenylsuccinic acid partial esters and partial amides, 4-nonylphenoxyacetic acid.

b) Nitrogen-containing compounds, for example:
i. Primary, secondary or tertiary aliphatic or cycloaliphatic amines and amine salts of organic and inorganic acids, for example oil-soluble alkylammonium carboxylates.

ii. Heterocyclic compounds, for example: substituted imidazolines and oxazolines.

c) Phosphorous-containing compounds, for example: amine salts of phosphoric acid partial esters or phosphonic acid partial esters, zinc dialkyldithiophosphates.

d) Sulfur-containing compounds, for example: barium dinonylnaphthalenesulfonates, calcium petroleumsulfonates.

Examples of viscosity index improvers are: polyacrylates, polymethacrylates, vinylpyrrolidone/methacrylate copolymers, polyvinylpyrrolidones, polybutenes, olefin copolymers, styrene/acrylate copolymers, polyethers.

Examples of pour point depressants are: polymethacrylate, alkylated naphthalene derivatives.

Examples of dispersants/surfactants are: polybutenylsuccinamides or -imides, polybutenylphosphonic acid derivatives, basic magnesium sulfonates and phenolates, calcium sulfonates and phenolates, and barium sulfonates and phenolates.

Examples of wear-resistant additives are: sulfur- and/or phosphorus- and/or halogen-containing compounds, such as sulfurised vegetable oils, zinc dialkyldithiophosphates, tritolyl phosphate, chlorinated paraffins, alkyl and aryl di- and tri-sulfides, triphenyl phosphorothionates, diethanolaminomethyltolyltriazole, di(2-ethylhexyl)aminomethyltolyltriazole.

The present invention also relates to the use of compounds of the formula I for stabilising organic material which is sensitive to oxidative, thermal and/or light-induced degradation, in particular natural or (semi)synthetic polymers or functional fluids, in particular thermoplastic polymers or elastomers, and lubricants. The compounds are, for example, particularly efficient as antioxidants in functional fluids, as mentioned above.

Advantageous and preferred compounds of the formula I, as described above, result in advantageous and preferred compositions.

The compounds of the formula I are prepared by methods known per se (cf., for example WO-A-88/08 420, DE-A-2 243 777):

The synthesis follows, for example, the scheme

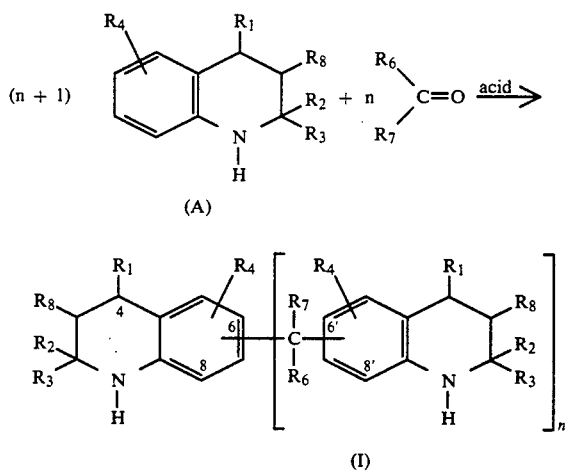

As described in DE-A-2 243 777, the reaction can lead to the formation of mixtures in which compounds of the formula I where n is 1,2 and 3 are present next to one another. The yield of main products can be largely regulated by means of reaction conditions and relative amounts of the starting materials. The mixtures formed can be separated by known processes (such as crystallisation, fractional distillation or chromatography) or, alternatively, advantageously used as such for the intended purpose.

In a particularly preferred embodiment, for example, 2,2,4-trimethyl-1,2,3,4-tetrahydroquinoline is used as the starting material and reacted with a carbonyl compound $R_6COR_7$ in the presence of a 1-2-fold excess of a mineral acid and 2-3% by weight of a nitrogen-containing base to give the compound of the formula I in which n is 1, $R_4$ and $R_8$ are hydrogen and $R_1$, $R_2$ and $R_3$ are methyl.

The starting compounds of the formula A are known or can be obtained by processes known per se, as described, for example, in U.S. Pat. No. 4,692,258 and U.S. Pat. No. 4,828,741.

The examples which follow illustrate the invention in more detail without, however, limiting it. All parts and percentages given therein—and also in the rest of the description—are by weight, unless stated otherwise.

EXAMPLE 1

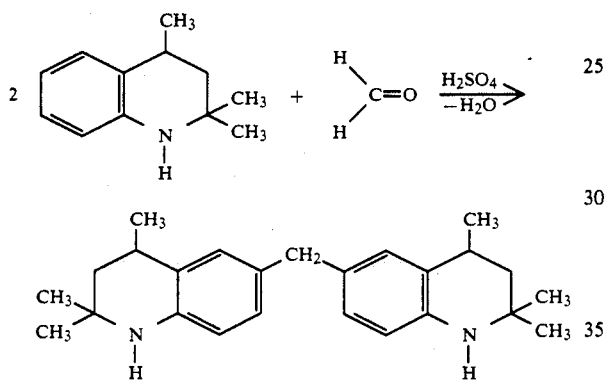

35.2 g (0.2 mol) of 2,2,4-trimethyl-1,2,3,4-tetrahydroquinoline are initially introduced into 100 ml of water at room temperature in a 300 ml sulfonating flask, resulting in two phases. After the dropwise addition of 10.2 g (0.1 mol) of concentrated sulfuric acid over a period of 15 minutes, a clear, brownish solution is formed with a slight evolution of heat. After cooling in an ice bath, 8.4 g (0.1 mol) of 36% formaldehyde solution are added dropwise over a period of 30 minutes. After stirring for one hour, the mixture is allowed to warm to room temperature. After stirring for another 16 hours, a brown crystalline paste is formed. This paste is taken up in 200 ml of toluene and brought to a pH slightly above the neutral point using dilute potassium hydroxide solution. The organic phase is washed with 300 ml of water until neutral. After drying over 10 g of $Na_2SO_4$, the mixture is filtered and the filtrate is evaporated to dryness on a rotary evaporator. Drying under a high vacuum for 2 hours gives 35.8 g (98.8% of theory) of a brown, resinous oil.

| Analysis: | found | calculated |
|---|---|---|
| C: | 82.7% | 82.2% |
| H: | 9.5% | 9.5% |
| N | 7.7% | 7.7% |

NMR measurements confirm the position of the methylene bridge.

EXAMPLE 2

Stabilisation test of an industrial oil against oxidative degradation (TFOUT: Thin Film Oxygen Uptake Test)

This test is a modified form of the Rotary Bomb Test for mineral oils (ASTM D 272). A detailed description can be found in C. S. Ku, S. M. Hsu, Lubrication Engineering 40 (1984) 75-83. The test oil is in this case a commercial motor oil of the ARAL RL 136/3 type. The additive to be tested (compound of the formula I) is tested for its stabilising effect in the oil in the presence of water (2%), an oxidised/nitrated gasoline fraction (4%) and a mixture of liquid metal naphthenates (4%) at an oxygen pressure of 6.1 bar and 160° C. The water and the two liquid catalysts for the test are obtained from the National Bureau of Standards (NBS) under the name Standard Reference Material 1817 together with a certificate for analysis. The test is complete when a clear break in the pressure/time diagram indicates the onset of oxidation at the end of the induction period (min.). A long induction period denotes a good stabilising effect of the additive. The results are summarised in Table 1.

TABLE 1

| Compound from Example | Amount added (% by weight) | Induction period (min.) |
|---|---|---|
| 1 | 0.75 | 289 |
| Reference | without additive | 146 |

What is claimed is:
1. A stabilized composition comprising
   (A) a lubricant or a functional fluid, and
   (B) an effective stabilizing amount of at least one compound of formula I

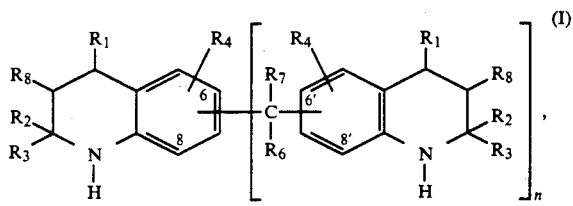

in which
$R_1$ is $C_1$-$C_{18}$alkyl, or $R_1$ together with $R_8$ are 1,4-butylene, $R_2$ and $R_3$, independently of one another, are $C_1$-$C_{18}$alkyl, phenyl or phenyl-$C_1$-$C_4$alkyl, or $R_2$ and $R_3$ together are tetramethylene, pentamethylene or hexamethylene, $R_4$ is hydrogen, halogen, nitro, $C_1$-$C_{24}$alkyl or a group —$OR_5$ where $R_5$ is hydrogen, $C_1$-$C_{18}$alkyl or benzyl, $R_6$ and $R_7$, independently of one another, are hydrogen, $C_1$-$C_{18}$alkyl, $C_2$-$C_{18}$alkyl which is interrupted by —S— or —O—, phenyl or phenyl-$C_1$-$C_4$alkyl, or $R_6$ and $R_7$ together are $C_4$-$C_{11}$alkylene, $R_8$ is hydrogen, $C_1$-$C_{18}$alkyl, and n is 1 or 2.

2. A composition according to claim 1, in which the organic material is a functional fluid.

3. A composition according to claim 1, in which the organic material is a lubricant or a hydraulic fluid.

4. A process for stabilizing a lubricant or functional fluid which process comprises
adding or applying to said lubricant or functional fluid an effective stabilizing amount of at least one compound of formula I

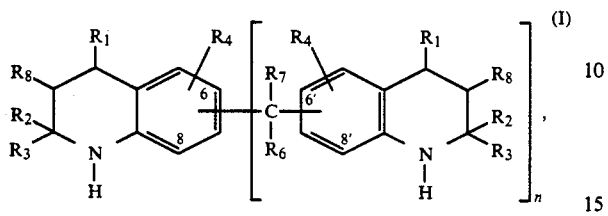

in which
$R_1$ is $C_1$-$C_{18}$alkyl, or $R_1$ together with $R_8$ are 1,4-butylene, $R_2$ and $R_3$, independently of one another, are $C_1$-$C_{18}$alkyl, phenyl or phenyl-$C_1$-$C_4$alkyl, or $R_2$ and $R_3$ together are tetramethylene, pentamethylene or hexamethylene, $R_4$ is hydrogen, halogen, nitro, $C_1$-$C_{24}$alkyl or a group —$OR_5$ where $R_5$ is hydrogen, $C_1$-$C_{18}$alkyl or benzyl, $R_6$ and $R_7$, independently of one another, are hydrogen, $C_1$-$C_{18}$alkyl, $C_2$-$C_{18}$alkyl which is interrupted by —S— or —O—, phenyl or phenyl-$C_1$-$C_4$alkyl, or $R_6$ and $R_7$ together are $C_4$-$C_{11}$alkylene, $R_8$ is hydrogen, $C_1$-$C_{18}$alkyl, and n is 1 or 2.

5. A process according to claim 4 for stabilizing a functional fluid.

6. A process according to claim 5 for stabilizing lubricant or hydraulic fluid.

* * * * *